(12) United States Patent
Martino

(10) Patent No.: US 6,540,766 B2
(45) Date of Patent: Apr. 1, 2003

(54) NOSTRIL DILATOR FOR HORSES

(75) Inventor: Nicholas Martino, Barrie (CA)

(73) Assignee: Tyson Shaver, Burnaby (CA)

( * ) Notice: Subject to any disclaimer, the term of this patent is extended or adjusted under 35 U.S.C. 154(b) by 22 days.

(21) Appl. No.: 09/832,040

(22) Filed: Apr. 11, 2001

(65) Prior Publication Data

US 2002/0151925 A1 Oct. 17, 2002

(51) Int. Cl.[7] ............................................. A61M 29/00

(52) U.S. Cl. ...................................................... 606/199

(58) Field of Search ............................ 606/204.45, 199, 606/191, 201, 198, 196; 158/200.24; 128/200.24

(56) References Cited

U.S. PATENT DOCUMENTS

| | | | | |
|---|---|---|---|---|
| 5,816,241 A | * | 10/1998 | Cook | 128/200.24 |
| 5,913,873 A | | 6/1999 | Blach et al. | |
| 5,922,006 A | * | 7/1999 | Sugerman | 606/204.15 |
| 6,017,357 A | | 1/2000 | Blach et al. | |
| 6,033,422 A | | 3/2000 | Blach et al. | |
| 6,228,101 B1 | * | 5/2001 | Stratton | 128/200.24 |
| 6,238,411 B1 | * | 5/2001 | Thorner | 606/199 |
| 6,270,512 B1 | * | 8/2001 | Rittmann | 128/207.18 |

* cited by examiner

Primary Examiner—Ismael Izaguirre
(74) Attorney, Agent, or Firm—McDermott, Will & Emery

(57) ABSTRACT

This invention is a nasal dilator (1) for dilating a first and a second nasal passage of a nose of an animal, including a first member (2) and a second member (4) for inserting in the nostrils of the animal and maintained in a spaced-apart relationship with attachment arms (8,10) to maintain the dilator in place.

6 Claims, 2 Drawing Sheets

NOSTRIL DILATOR FOR HORSES

FIELD OF THE INVENTION

This invention relates to a nostril dilator for use with animals. In particular, this invention relates to a nostril dilator for use with race horses.

BACKGROUND OF THE INVENTION

There are many situations where it is important to ensure that animals such as horses and humans, have a maximum supply of oxygen. In such cases, it is necessary to ensure that the nostrils of the animal are dilated to their fullest.

In horse racing, the horse requires a maximum supply of oxygen in order to ensure that the heart pumps oxygen-rich blood to the muscles. While racing, a horse's nostrils tend to flare such that the passage of air is often impeded.

Various methods and apparatus have been devised to keep a horse's nostrils open. The most common approach is by the use of nasal supports or pads which are applied to the outer surface of the horse's nostrils. These supports exert a downward pressure on the nostrils to keep them open. Examples of such devices can be found in U.S. Pat. Nos. 6,033,422; 6,017,357; and 5,913,873.

However, such nasal supports or pads do not completely ensure that the horse's nostrils remain open. In some cases the horse cannot sweat properly, or the nasal supports fall off. Furthermore, the nasal supports or pads can only be used once because they are kept in place with adhesive.

Where no measures are taken to keep a horse's nostrils open by means of nasal suppports or pads or the like, the lungs are prone to bleed as the nostrils open and close.

There are other situations where it is important to keep an animal's nostrils open. One such example is during surgery of an animal.

It would be advantageous to use a nostril dilator which could be placed inside the horse's nostrils to keep them open.

SUMMARY OF THE INVENTION

It is an object of the invention to provide a nostril dilator which improves the passage of oxygen for a race horse.

According to one embodiment of the invention, there is provided a nostril dilator for use with an animal, comprising a first member for inserting in the first nostril of an animal, a second member for inserting in the second nostril of an animal a third member connecting said first and second members, the third member maintaining said first and second members in a spaced-apart relationship, and attachment means connected to said first and second members for maintaining said first and second members in the nostrils of the animal.

The first member has an upper arm and a lower arm in a generally spaced-apart relationship and the said second member has an upper arm and a lower arm in a generally spaced-apart relationship.

Attachment means comprises a first arm which is connected to the first member, and a second arm connected to the second member, said first arm and second arm converging to meet.

According to one embodiment the two arms meet to form a hook to which at least one strap is used to attach to the harness of the animal. The strap preferably is elastic and could be a bungee cord or the like.

Advantages of the invention are:

BRIEF DESCRIPTION OF THE DRAWINGS

Embodiments of the invention will now be described by way of example with reference to the following drawings in which.

DETAILED DESCRIPTION

Figure 1:
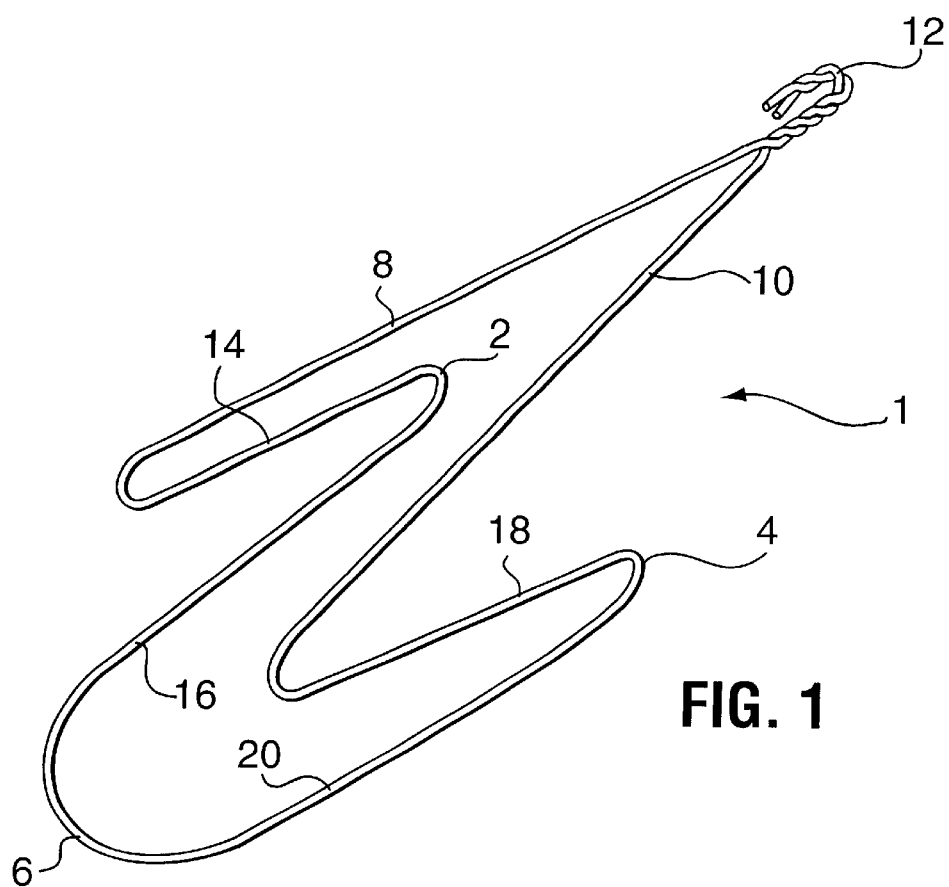
FIG. 1 is a perspective view of a nostril dilator according to one embodiment of the invention.
Figure 2:
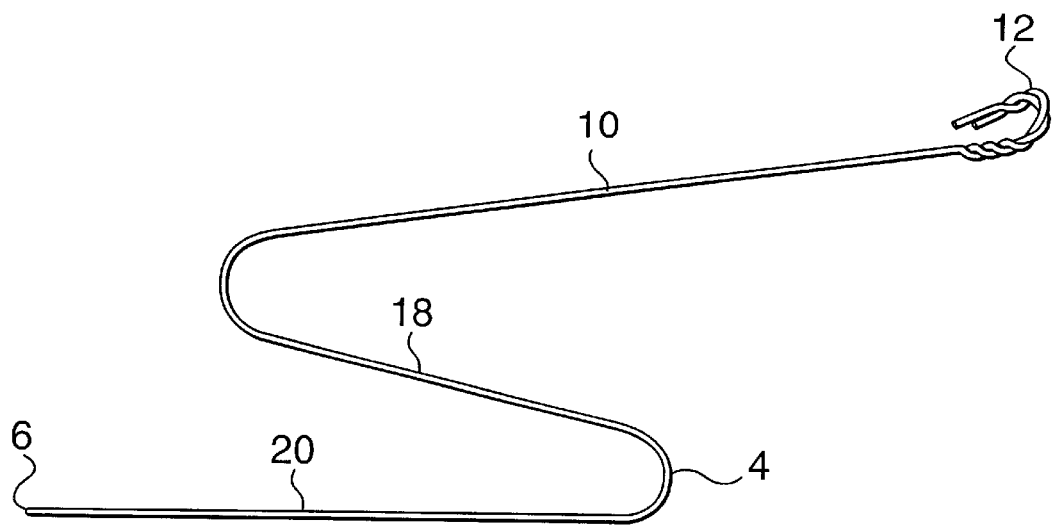
FIG. 2 is a right side view of the nostril dilator of FIG. 1.
Figure 3:
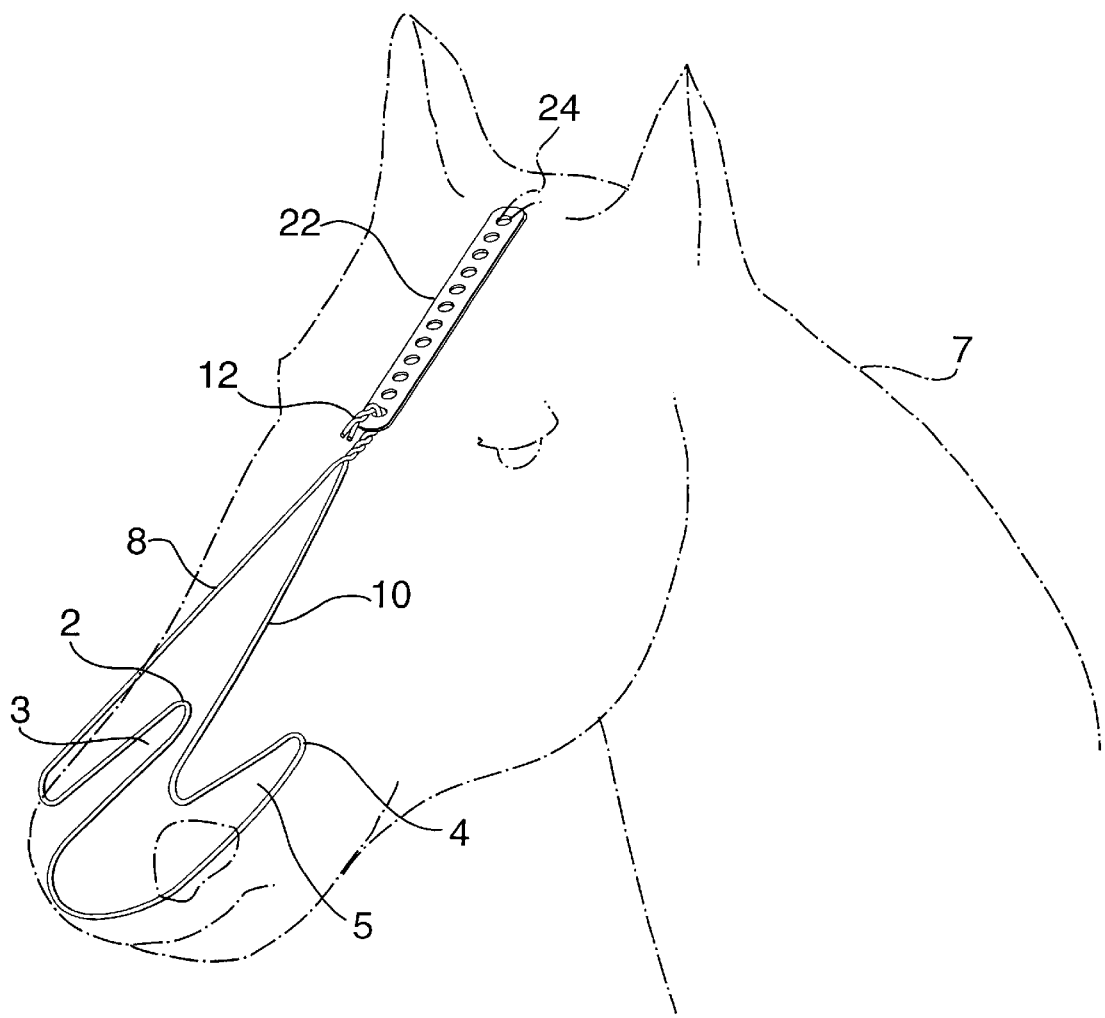
FIG. 3 is a perspective view of the nostril dilator of FIG. 1 showing the use of the nostril dilator with a horse.

Referring to the Figures, there is shown a nostril dilator 1 having a first member 2 which is inserted in the first nostril 3 of an animal. A second member 4 is provided for insertion in the second nostril 5 of the animal 7. A third member 6 connects the first member 2 and second member 4 and maintains the first member 2 and second member 4 in a spaced-apart relationship. Attachment means is provided comprising a first arm 8 connected to the first member 2, and a second arm 10 connected to the second member 4. The first arm 8 and the second arm 10 are connected at one end to form a hook 12.

The first member 2 has an upper arm 14 and a lower arm 16 in a spaced-apart relationship which maintain the first nostril 3 in a generally open position.

The second member 4 has an upper arm 18 and a lower arm 20 in a spaced-apart relationship which maintain the second nostril 5 in a generally open position.

According to one embodiment of the invention, the entire nostril dilator 1 may be formed from a single piece of wire or other suitable material.

According to another embodiment of the invention, the hook 12 could be attached to a flat strap 22 with spaced-apart holes or a bungee cord, or other suitable device for attaching to the harness 24 of a horse 7.

Referring to the Figures, in use the nostril dilator 1 is placed over the muzzle of an animal 7 such that the first member 2 is inserted in the first nostril 3 of the animal 7 while the second member 4 is inserted in the second nostril 5 of the animal 7. The third member 6 rests between the nose and the upper lip of the animal 7. The first arm 8 and the second arm 10 rest on the bridge of the nose of the animal 7.

The first member 2 has an upper arm 14 and a lower arm 16 in a spaced-apart relationship which maintain the first nostril 3 in a generally open position.

The second member 4 has an upper arm 18 and a lower arm 20 in a spaced-apart relationship which maintain the second nostril 5 in a generally open position.

The nostril dilator 1 is maintained in place by attachment means comprising a first arm 8 connected to the first member 2, and a second arm 10 connected to the second member 4. The first arm 8 and the second arm 10 are connected at one end to form a hook 12. At least one strap 22 or other suitable device could be attached to the first arm 8 and second arm 10 and then to the harness 24 of the animal. The strap should preferably be elastic and could be a bungee cord. The elastic nature of the bungee cord 22 will ensure that the dilator 1 remains generally snug in the nostril of the animal 7.

It will be understood by the person skilled in the art that a number of modifications and variations could be made without departing from the scope or intention of the invention.

I claim:

1. A nostril dilator for use with animal, comprising:
   (a) a first member for inserting in the first nostril of an animal;
   (b) a second member for inserting in the second nostril of an animal;
   (c) a third member connecting said first and second members, said third member maintaining said first and second members in a spaced-apart relationship; and
   (d) attachment means connected to said first and second members for maintaining said first and second members in the nostrils of the animal, wherein said first member has an upper arm and a lower arm in a generally spaced-apart relationship, and wherein said second member has an upper arm and a lower arm in a generally spaced-apart relationship.

2. A nostril dilator for use with animal, comprising:
   (a) a first member for inserting in the first nostril of an animal;
   (b) a second member for inserting in the second nostril of an animal;
   (c) a third member connecting said first and second members, said third member maintaining said first and second members in a spaced-apart relationship; and
   (d) attachment means connected to said first and second members for maintaining said first and second members in the nostrils of the animal, wherein the attachment means comprises a first arm which is connected to the first member, and a second arm connected to the second member, and wherein said first arm and second arm converge to meet.

3. The nostril dilator according to claim 2 wherein the first arm and second arm meet to form a hook.

4. A nostril dilator for use with animal, comprising:
   (a) a first member for inserting in the first nostril of an animal;
   (b) a second member for inserting in the second nostril of an animal;
   (c) a third member connecting said first and second members, said third member maintaining said first and second members in a spaced-apart relationship; and
   (d) attachment means connected to said first and second members for maintaining said first and second members in the nostrils of the animal, wherein the attachment means has at least one strap for attachment to a harness of the animal.

5. The nostril dilator according to claim 4 wherein the strap is elastic.

6. The nostril dilator according to claim 5 wherein the strap is a bungee cord.

* * * * *